United States Patent [19]

Pitha

[11] 4,371,673
[45] Feb. 1, 1983

[54] WATER SOLUBLE FORMS OF RETINOIDS

[75] Inventor: Josef Pitha, Baltimore, Md.

[73] Assignee: The United States of America as represented by the Secretary of the Department of Health and Human Services, Washington, D.C.

[21] Appl. No.: 170,570

[22] Filed: Jul. 21, 1980

[51] Int. Cl.³ .................... C08G 69/48; C08B 37/16
[52] U.S. Cl. ...................................... 525/426; 424/78; 525/417; 525/419; 527/306; 527/309; 527/312; 527/313; 536/112
[58] Field of Search ............ 525/426, 419, 417; 424/78; 536/112; 527/306, 309, 312, 313

[56] References Cited

U.S. PATENT DOCUMENTS

| | | | |
|---|---|---|---|
| 3,130,126 | 4/1964 | Noval | 424/78 |
| 3,441,526 | 4/1969 | Zilkha et al. | 525/426 |
| 4,274,985 | 6/1981 | Szejtli et al. | 260/9 |

OTHER PUBLICATIONS

Journal of Biological Chemistry, 248, No. 17, pp. 6246–6247, (1973), Machida et al.
Journal of the American Chemical Society, 83, pp. 2312–2320, (1961), Schlenk et al.
Acta Chemica Academiae Scientarium Hungaricae, 99, pp. 447–452, (1979), Szejtli et al.
Proceedings of the National Academy of Science, U.S.A., 76, pp. 2204–2208, (1979), Takese et al.
Proceedings of the National Academy of Science, U.S.A., 75, pp. 3867–3870, (1978), Ryser et al.
Journal of the National Cancer Institute, 62, pp. 1261–1264, (1979), Fung et al.

*Primary Examiner*—Harold D. Anderson
*Attorney, Agent, or Firm*—Holman & Stern

[57] ABSTRACT

Two types of water soluble complexes of retinoids possessing vitamin A-like biological activity and use but of lower toxicity are disclosed: (A) Cyclodextrin complexes of retinoid-polymers and (B) Complexes of retinoids with ether type derivatives of cyclodextrins.

21 Claims, 3 Drawing Figures

WATER SOLUBLE FORMS OF RETINOIDS

BACKGROUND OF THE INVENTION

1. Field of the Invention

This invention relates to water soluble Retinoid complexes and a method for their preparation.

2. Description of the Prior Art

Retinoids, which are characterized by the general formula

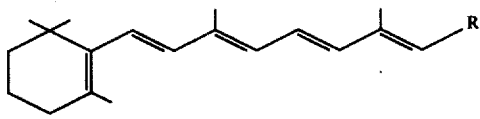

generally possess vitamin A activity and are, therefore, of nutritional importance. In addition, they possess therapeutic value in the prevention and treatment of neoplasias and of skin diseases. These compounds, which are highly lipophilic, are found to be unevenly distributed after assimilation into the bodies of humans and other animals. As a consequence, when administered in high doses, the concentration of retinoids in some organs rapidly reaches a toxic level. M. B. Sporn, et al., *Federation Proceedings*, 35, 1332–38 (1976) and W. Bollag, *Cancer Chemotherapy Reports*, 55, 53–8 (1971). In view of the positive effects shown by such vitamin A related compounds, particularly in the prophylactic effects exhibited against the development of epithelial cancer in animals exposed to chemical carcinogens and their demonstrated inhibition of certain transplantable tumors in vivo and in vitro, it would be expected that structural modification of the basic retinoid structure, shown above, would offer great promise and an avenue of research to be pursued in the treatment and prevention of cancer. In an attempt to identify compounds with improved biological activity, unique pharmacodynamics or lower systemic toxicity, new retinoids are being synthesized and screened for their biological activity. It has been demonstrated that modifications in the polarity of some drugs frequently alters their in vivo tissue distribution, resulting in some cases, in lower toxic effects. It is the basic lipophilic character of retinoids in general, however, which determines in large part the toxicity of the compounds as a class.

SUMMARY OF THE INVENTION

The present invention overcomes many of the problems of the prior art. Namely, to diminish the toxic effects of retinoids, one approach is to alter the molecular structure such that toxicity to specific organs, or cells generally, is diminished. An alternate approach is to modify the molecular structure of the retinoid such that its concentration and/or distribution in the organism is varied. The present invention involves this latter approach. The retinoid complexes of the instant invention gain hydrophilic character at the expense of the lipophilic nature which characterizes the free retinoid compounds. Thus, by complexation of a retinoid, as described below, water solubility is markedly increased in comparison to the free, or non-complexed, retinoid. The decreased lipophilic character and increased hydrophilic character of the complexes of the present invention permit the alteration both in the manner in which a retinoid may be administered as well as the concentration or overall amount of such retinoid to be varied. The complexes of the present invention, having lower fat solubility than the free retinoids, tend less to concentrate in many organs in the body. Higher concentrations and larger amounts of a retinoid complex may be administered as compared to the free retinoid, thus, diminishing, or largely eliminating, the toxic side effects associated generally with retinoids. In topical application, the complexes of the present invention, which are of macromolecular character, have also been found to distribute less rapidly than those retinoids from which they are derived.

The complexes of the present invention have been demonstrated to undergo slow hydrolysis to the original retinoid. The combination of water solubility and slow hydrolysis, when administering such complexes to living organisms, permits specific organs to be targeted while avoiding overloading the natural system. The retinoid complexes herein described have also been found to be compatible with saline solutions, thus being ideally suited for the preparation and administration of isotonic solutions suitable for injection.

DESCRIPTION OF THE PREFERRED EMBODIMENTS

The present invention obtains the desired solubility of retinoid compounds by providing two types of cyclodextrin complexes of retinoids: (1) cyclodextrin complexes of retinoid-polymers and (2) cyclodextrin complexes of free retinoids.

Cyclodextrin Complexes of Retinoid-Polymers

Figure 1:
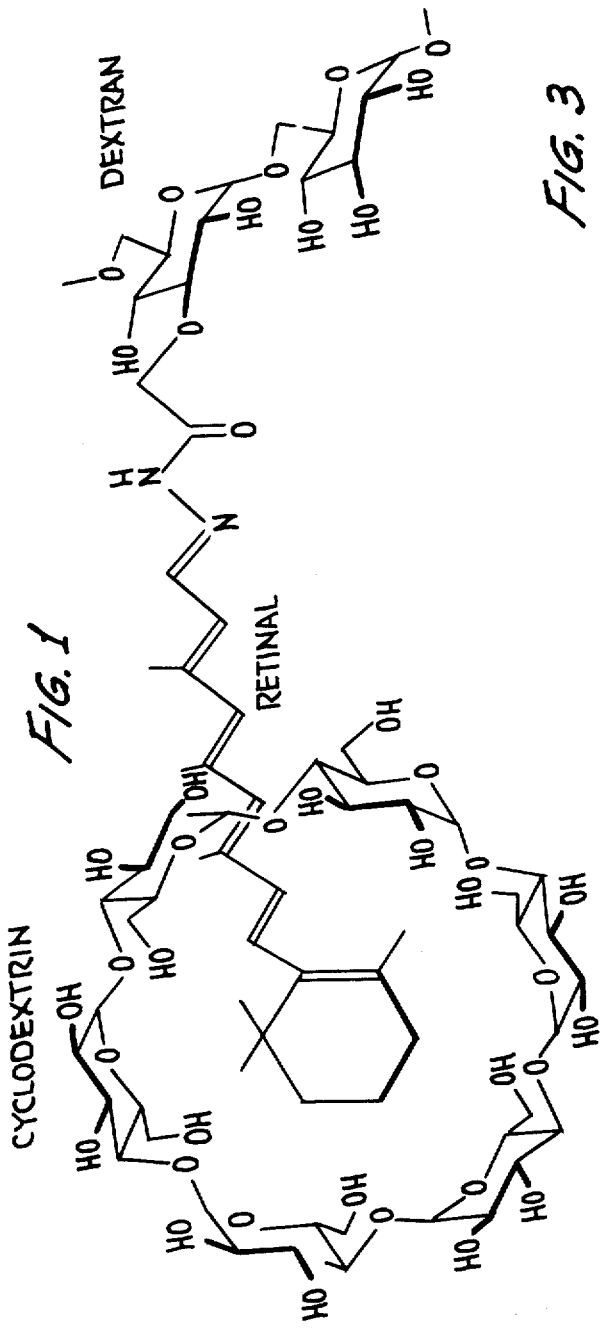
FIG. 1 is a schematic structural formula of a water-soluble retinal-dextran molecule complexed with α-cyclodextrin.

The first type of retinoid complex involves modification of a retinoid molecule to form a covalent bond between the terminal group of the retinoid and a reactive group of a polymer. The structure of such a retinoid-polymer is depicted in FIG. 1.

The factors which determine an appropriate polymer include: (a) the presence of functional groups which permit the formation of one or more covalent bonds to retinoid molecules, (b) the presence of functional groups which promote solubility in water or aqueous solutions and (c) the overall effect which such compounds would have on living organisms.

The first factor depends, in part, on the nature of the terminal functional group R (as shown in the above structural formula). The functional groups which R most frequently comprise include aldehyde, alcohol and carboxyl groups. A variety of polymeric materials could be selected considering the scope of the reactions which these groups (R) are capable of entering into. A second desirable feature of the functional groups present in the polymer is that such groups impart or improve water solubility. Such groups would tend, therefore, to be ionic or polar in nature. The preferred groups would include carboxyl, hydroxyl, amine, amide, carboxymethyl, etc. It is, however, not necessary that either very many of these groups be present, if at all, nor that they be present to the exclusion of other groups. While such groups improve the water solubility of the retinoid complex, water solubility is also imparted by the nature and structure of the cyclodextrin employed. The type of polymer employed must also be selected with a view to its ultimate biological use. If the complex is intended to be used in vivo, the polymer itself must not produce any toxic or detrimental side effects to the organism to which it is being administered. This is of some concern, since many of the retinoid-polymer complexes tested have demonstrated a tendency to hydrolyze. Indeed, this is one of the main benefits accruing to the use of the instant invention, i.e., the slow hydrolysis of the complex to form the free retinoid.

Among the polymeric materials which seem most suitable in the present invention are polysaccharides, their derivatives and polyamino acids. Among the polysaccharides suitable for use in the present invention, dextrans seem ideally suited, having an appropriate combination of molecular weight and number and type of polar groups to impart the desired hydrophilic character to the retinoid-polymer complex.

The polysaccharides may also be converted to derivatives, either to alter the hydrophilicity of the material or to provide functional groups which may allow more facile reaction with the terminal groups of the retinoid compound. Conversion, for instance, of dextran into carboxymethyl dextran, may be viewed conceptually as replacing a hydroxyl group with a carboxymethyl group. While modifying the solubility characteristics of the polymer somewhat, this also permits the formation of other intermediates by means of appropriate reactions of one or more of the carboxyl groups. Thus, the carboxyl groups of carboxymethyl dextran may be partially or totally converted to hydrazide groups. By such a transformation, retinoids having a terminal group which is a carbonyl group, such as retinal or one or more of its derivatives, may be converted to a hydrazone. Similar hydrazides may be prepared from other appropriate polymeric materials containing a carboxyl or ester group. Amino acids, polyamino acids and derivatives thereof prove useful in this respect. For example, hydrazides derived from polyglutamates, such as poly-$\gamma$-benzyl-L-glutamate, has been condensed with retinal to produce suitable retinoid-polymers. Derivatives of polyamino acids and their esters have been shown also to form suitable hydrazides. Thus, a polyamino acid ester such as poly-$\gamma$-benzyl-L-glutamate may be partly condensed with an excess of an aminoalcohol such as 3-aminopropanol, which subsequently undergoes hydrazinolysis of the ester groups to provide the corresponding hydrazide, polyglutamyl(hydrazide-3-hydroxylpropylamide), which may subsequently be condensed with retinal or a derivative thereof.

Retinoid-polymers which are prepared from hydrazones of retinal or its derivatives, are typically prepared by initially forming the hydrazide of the polymeric material in aqueous solution. The carboxyl or ester containing polymer is thus dissolved in water, aqueous hydrazine added to the solution and the pH adjusted with hydrochloric acid to a value below 7. A suitable condensing agent, such as 1-ethyl-3(3-dimethylaminopropyl)-carbodiimide, is added while maintaining the pH between 4 and 6. After several repetitions of this process, the solution is then exhaustively dialyzed, cleared by centrifugation and freeze-dried. The condensation with retinal may then be effected by dissolving the powdered hydrazide in a sodium acetate solution (pH of approximately 6) and adding thereto retinal or one of its derivatives. The mixture is then stirred in the dark under a nitrogen atmosphere at room temperature. Thereafter, the mixture is dialyzed over night and centrifuged.

The retinoid-polymer complex may be formed by subsequently combining the retinoid-polymer with one or more appropriate cyclodextrins in aqueous solution or may be formed in the same step in which the retinoid-polymer is produced. In the latter case, a suitable cyclodextrin or mixture of cyclodextrins is added to an aqueous solution of the polymeric material with stirring. The retinoid compound is subsequently added and stirring is continued for as long as three days in the dark at room temperature under a nitrogen atmosphere. The mixture is then dialyzed over night against an isotonic solution.

Cyclodextrins, suitable for use in preparing the retinoid-polymer complexes of the instant invention include $\alpha$-cyclodextrin, $\beta$-cyclodextrin, $\gamma$-cyclodextrin and derivatives of these cyclodextrins. Suitable derivatives of these cyclodextrins are alkoxy or ether derivatives. Examples of which are dodecakis-2,6-O-methyl-$\alpha$-cyclodextrin; tetradecakis-2,6-O-methyl-$\beta$-cyclodextrin; hexadecakis-2,6-O-methyl-$\gamma$-cyclodextrin, and a tetradecakis ether formed between $\beta$-cyclodextrin and monomethyloligoethylene glycol.

The following examples are provided to illustrate the preparation of carboxymethyldextran, a hydrazide of carboxymethyldextran, a retinal hydrazone of carboxymethyldextran and a cyclodextrin complex of this hydrazone. These examples are intended to provide details to one skilled in the art of how to prepare these and related embodiments of the instant invention. They are not intended to limit the scope of the invention. It should be added that preparation of related retinoid-polymers, and complexes thereof, employing amino acids, polyamino acids and their derivatives in which retinoic acid or its derivatives are used as the retinoid compound, may be carried out in a manner similar to that disclosed herein and are fully within the purview of the skilled artisan.

PREPARATION OF CARBOXYMETHYLDEXTRAN

To a solution of dextran (average mol. wt. 40,000, 5 g in 5 ml water) were added 38 mL of 40% sodium hydroxide and 27 g of chloroacetic acid, and the suspension was stirred for 12 hr at room temperature. After repeating this process twice, the solution was dialyzed exhaustively against water and freeze-dried. The product (9.4 g) was found to contain 4.4 $\mu$moles of carboxylic group per mg (determined from the nitrogen content of the ammonium salt of the product).

PREPARATION OF CARBOXYMETHYLDEXTRAN HYDRAZIDE

Part of the carboxyl groups of the carboxymethyldextran, prepared as indicated above, were converted to hydrazide groups by adding aqueous hydrazine solution (12 g hydrazine hydrate, 85%, neutralized with concentrated hydrochloric acid to pH 5) to carboxymethyldextran (2 g) followed by the addition of 1-ethyl-3(3-dimethylaminopropyl)carbodiimide (1 g). During the reaction (50 min) the pH was kept in the range 4.5–5.0. The process was repeated two additional times, and the solution was dialyzed exhaustively against water, cleared by centrifugation and freeze-dried. The resulting powder contained 7.4% nitrogen indicating the presence of 2.6 μmoles of hydrazide groups per mg.

PREPARATION OF A CYCLODEXTRIN COMPLEX OF RETINAL-CARBOXYMETHYLDEXTRAN HYDRAZONE

For the combined condensation of retinal with the hydrazide of carboxymethyldextran and formation of the complex a solution of the above described hydrazide (270 mg dissolved in 35 mL of 5 mM sodium acetate, pH 6) was mixed with α-cyclodextrin (2.63 g) and β-cyclodextrin (350 mg) and the mixture stirred for 1 hr at 23° C. before adding retinal (80 mg) and subsequent stirring for 60 hr in the dark, under a nitrogen atmosphere at room temperature. The mixture was then dialyzed overnight against 1 L of isotonic, pH 7.2 phosphate buffer containing (per 1 L water): 8 g NaCl, 2.2 g $Na_2HPO_4.7H_2O$, 0.2 g $KH_2PO_4$ and 0.2 g KCl. After centrifugation (10,000 rpm, 10 min), the clear yellow solution of retinal-dextran exhibited an absorbance spectrum with a maximum which varied within the range of 360 to 385 nm in different preparations. The concentration of retinal in the complex was estimated by comparison of the absorbance at the peak of the absorbance spectrum with the absorbance of free retinal in ethanol at 380 nm. The solutions of retinal-dextran were found to contain between 0.42 and 0.7 μmoles retinal per mg dextran and an overall concentration of retinal equivalent of up to 1000 μg (3.52 μmoles) per mL. Clear solutions of retinal-dextran complex containing 2000 μg of retinal per mL could be prepared by enclosing the solution to be concentrated in a dialyzing bag and embedding the bag in dry Sephadex and incubating at 4° C. until the volume was reduced to the desired value. Freezing the solution resulted in an irreversible precipitation of the complex; however, it was possible to store the solution in the dark at 4° C. for more than a month without precipitation or loss of biological effects.

The solubility of the retinal-carboxymethyldextran complex in isotonic buffered saline solution was in the range of 600 to 1,000 μg/ml. This is a substantial increase in solubility in comparison to the solubility of free retinal in the same buffer solution; the latter exhibits solubility below the limits of detection, that is, less than 0.01 μg/ml.

RETINOID COMPLEXES

It has been discovered that by appropriately selecting a derivatized cyclodextrin, it is unnecessary to prepare a retinoid-polymer compound preliminary to, or concurrent with, the preparation of the complex. This greatly simplifies the process of dissolving a retinoid. Thus, to prepare a solution of the cyclodextrin retinoid complex, it is merely necessary to add the components, retinoid and cyclodextrin, with stirring to an aqueous medium, such as a saline or isotonic solution, at room temperature. If one has a suitable cyclodextrin available, it is unnecessary to synthesize the cyclodextrin retinoid-polymer. If, however, one of the more suitable cyclodextrins is not available or if a structurally modified retinoid is used which does not provide a sufficiently high solubility with a suitable cyclodextrin, the preparation of a cyclodextrin retinoid-polymer may still be preferred.

Among the cyclodextrins which have proved to be most suitable are α-, β- and γ-cyclodextrin and derivatives thereof. Suitable derivatives include compounds in which some of the hydroxyl groups have been replaced with methoxy, ethoxy and 2-hydroxyethoxy groups. Examples of suitable compounds include α-cyclodextrin, β-cyclodextrin, γ-cyclodextrin, dodecakis-2,6-O-methyl-α-cyclodextrin, tetradecakis-2,6-O-methyl-β-cyclodextrin, hexadecakis-2,6-O-methyl-γ-cyclodextrin and tetradecakis-2,6-O-ethyl-β-cyclodextrin. A similar ether of β-cyclodextrin has been prepared with monomethyloligoethylene glycol which also solubilizes retinoids, demonstrating that ethylene glycol ethers are quite suitable.

Some examples of the solubility obtained for retinoid-dextrin complexes of the present invention in physiologically acceptable solutions are presented in Table 1. It may be noted that while the solubility of a complex of one retinoid with a particular cyclodextrin may not be great, the solubility of a complex of another retinoid, using the same cyclodextrin, may be increased several orders of magnitude.

TABLE 1

Direct Solubilization of Retinoids by Cyclodextrins and their Derivatives

| | Solubility of retinoid (μg/ml) in physiological buffered saline (NaCl, 8 g/L; $Na_2HPO_4.7H_2O$, 2.2g/L; KCl, 0.2 g/L and $KH_2PO_4$, 0.2 g/L) | |
|---|---|---|
| Solubilization agent added | retinal | retinoic acid |
| none | <1 | 20 |
| α-cyclodextrin, 50 mg/ml | 4 | 140 |
| β-cyclodextrin, 17 mg/ml | 2 | 2000 |
| γ-cyclodextrin, 50 mg/ml | 1 | 130 |
| dodecakis-2,6-O—methyl-α-cyclodextrin, 25 mg/ml | 7 | 460 |
| tetradecakis-2,6-O—methyl-β-cyclodextrin, 50 mg/ml | 570 | 460 |
| hexadecakis-2,6-O—methyl-γ-cyclodextrin, 25 mg/ml | 4 | 140 |

As Table 1 indicates, there is considerable variation in the amount of retinoid which may be solubilized by the present method, although in all cases the cyclodextrin-complexes are more soluble than the free retinoid. The precise amounts of retinoid, cyclodextrin and aqueous medium may be determined by the practitioner in each situation. Based, however, on experiments with a number of cyclodextrins and retinoids, up to approximately 15 mg of retinoid may require as much as 100 mg of cyclodextrin per ml of solution. Generally, there is a direct correlation between the amount of cyclodextrin and the amount of retinoids dissolved. Again, this is very much dependent on the structures of each, as is indicated by the data presented in Table 1.

BIOLOGICAL EFFECTS OF CYCLODEXTRIN RETINOID-POLYMER AND CYCLODEXTRIN RETINOID COMPLEXES. (IN VIVO STUDIES)

Studies were undertaken to determine whether the chemical modification of retinoids to polymer-linked water soluble forms alter its biological activities. Specifically, the vitamin A-like activity of the mixed α-, β-dextrin complex of retinal-carboxymethyldextran hydrazone was tested on rats made vitamin A-deficient. The "animals" referred to herein should be construed as meaning rats.

To prepare the rats for dietary studies, male weanling albino rats of the Holtzman string were fed a vitamin A-deficient diet until a weight plateau was reached. A cyclic program was then begun in which the rats which were provided with the deficient diet were supplemented with retinoic acid at a rate of 2 μg per g. This was continued for 18 days followed by 10 days of the original deficient diet. At the termination of the fourth 18-day period in which the rats were fed the retinoic acid supplemented diet, the rats were fed for 7 days with the deficient diet and then used in two types of experiments: (a) Studies of the resorption of retinal-carboxymethyldextran hydrazone from the gastrointestinal tract and (b) studies of growth support for avitamineosis. The results of the resorption studies (a) were determined by spectrophotometrically analyzing for retinol in the serum or liver. The vitamin A-like activity of the complexes of the present invention (b) was evaluated by comparison of survival rates of a control group, those fed a cyclodextrin complex of a retinoid-polymer and those fed a free retinoid derivative.

The results are summarized in Table 2.

TABLE 2

Vitamin A-like activity of the retinal-dextran complex measured by the survival of rats fed vitamin-A deficient diet

| Treatment[a] | No. of days on vitamin A-deficient diet | No. of surviving animals/total |
|---|---|---|
| Experiment 1 | | |
| Retinyl acetate | 35 | 3/3 |
| Retinal-dextran complex | 35 | 3/3 |
| Experiment 2 | | |
| Control | 28 | 0/4[b] |
| Retinyl acetate | 28 | 4/4 |
| Retinal-dextran complex | 28 | 4/4 |
| Experiment 3 | | |
| Control | 31 | 0/3[c] |
| Retinoic acid | 31 | 0/3[d] |
| Retinal-dextran complex | 31 | 3/3[e] |

[a]The control rats received 0.2 mL of cottonseed oil intraperitoneally while the treated animals received 100 g of retinyl acetate or retinoic acid in 0.2 mL cottonseed oil or retinal-dextran complex (100 μg of retinal equivalent) in 0.2 mL water. Subsequently, the rats received a vitamin A-deficient diet for periods indicated in the Table and their survival was followed.
[b]The animals died on days 7, 9, 14 and 15, respectively.
[c]The animals died on days 16, 18 and 23, respectively. Serum retinol was not detectable.
[d]The animals died on days 14, 28 and 30, respectively. Serum retinol was not detectable.
[e]Levels of retinol were 3.1, 3.1 and 9.2 μg/100 mL in serum and 0.08, 0.11 and 0.11 μg/g in livers of 3 rats after 31 days on a vitamin A-deficient diet.

In a series of experiments, the resorption of the complex from the gastrointestinal tract was assessed. Retinol was detected in both the serum and liver of vitamin-A deficient rats within two hours after the oral administration of 100 μg of retinyl acetate. In contrast, the administration of an equivalent amount of retinal-carboxymethyldextran hydrazone complex was not followed by the appearance of detectable retinol in either the serum or the liver.

In the second series of experiments, compared in Table 2, the retinal-carboxymethyldextran complex was administered intraperitoneally and the survival of the vitamin A-deficient rats was followed during the 28 to 35 days of a vitamin A-deficient diet. It is clearly evident that rats which received the retinal-dextran complex survived as well as those which received retinyl acetate. In contrast, the control rats as well as those rats which received retinoic acid (Experiment 3) died. Thus, it appears that the retinal-carboxymethyldextran hydrazone complex, though apparently not efficiently absorbed from the gastrointestinal tract clearly exhibits vitamin A-like activity when given intraperitoneally. Furthermore, though speculative, it seems that a retinol-like compound is generated in vivo from the retinal-carboxymethyldextran complex since small, but significant amounts of retinol were detected in the serum and livers of the treated animals.

IN VITRO STUDIES

Certain retinoids are known to demonstrate inhibitory effects in the proliferation of malignant cells in culture. The potency of the cyclodextrin complex of retinal-carboxymethyldextran hydrazone, being a water soluble complex, was compared to the free-retinoid. For this assay, S91 Melanoma cells were employed since they have been shown to be sensitive to the growth inhibitory effects of retinoids.

TABLE 3

Effects of retinal, retinal-dextran complex and dextran on S91 melanoma cell proliferation

| Treatment[a] | No. of cells on Day 6 (*10^−6) | Percentage of growth inhibition[b] |
|---|---|---|
| Control | 5.38 ± 0.12 | 0 |
| Retinal, 0.2 μM | 3.87 ± 0.21 | 28 |
| 0.2 μM | 2.62 ± 0.02 | 52 |
| Retinal-dextran, 0.2 μM | 5.31 ± 0.18 | <10 |
| 1.0 μM | 5.10 ± 0.05 | <10 |
| 10.0 μM | 0.86 ± 0.03 | 84 |
| Tetradecanal-dextran, 5 μM | 5.48 ± 0.13 | <10 |
| 50 μM | 5.32 ± 0.06 | <10 |
| Hydrazide of carboxy- 1 μg/mL methyldextran, 5 μg/mL | 5.43 ± 0.15 | <10 |
|  | 5.29 ± 0.19 | <10 |
| Retinal 0.2 μM + Hydrazide of carboxymethyldextran, 1 μg/mL | 3.82 ± 0.08 | 30 |
| Retinal 1.0 μM + Hydrazide of carboxymethyldextran, 5 μg/mL | 2.29 ± 0.13 | 57 |

[a]Cells were plated at 3 × 10^4 cells per dish in 6-cm diameter dishes in growth medium alone or supplemented with the various compounds. Medium was chaged on Day 3. The cells were treated for 6 days and they were detached and counted. [b]Percentage of growth inhibition was determined as described in the Experimental section.

The results are summarized in Table 3. The table includes data at various concentrations since high concentrations of certain retinoids have been shown to cause non-specific, detergent-like toxic effects. Decreased plating efficiency and cell lysis are considered indications of cytotoxic effects. S-91 Melanoma cells were exposed to various concentrations of retinoids and retinal was observed to cause cell lysis within 24 hours of initial exposure of concentrations as low as 10 μM, and plating efficiency was decreased by about 50% at 4 μM.

The highest non-cytotoxic dose of retinal was observed to be 2 μM. In contrast, cell lysis occurred at concentrations of the retinal moiety only at concentrations in excess of 500 μM when the cyclodextrin complex of retinal-carboxymethyldextran was employed. In this instance, plating efficiency was reduced by about 50% at a concentration of 160 μM and was not cytotoxic at 40 μM. The significant inhibition values observed with the cyclodextrin retinal-carboxymethyldextran complex is apparently caused by the retinal moiety since a corresponding cyclodextrin complex of tetradecanal-carboxymethyldextran hydrazone was found to be non-inhibitory at a concentration of 100 μM of the tetradecanal moiety. This was the highest concentration which could be obtained in a buffered saline solution.

Figure 2:
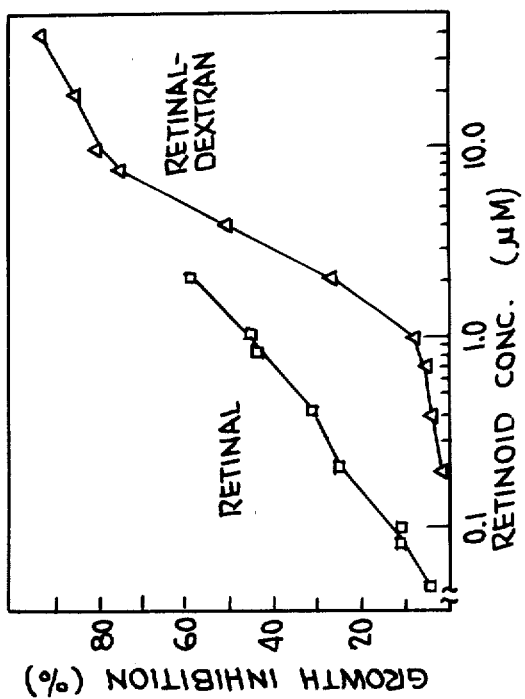
FIG. 2 graphically illustrates dose-response relationships of retinal and dextrin-complexed retinal-dextran, respectively, in the growth inhibition of S-91 melanoma cell proliferation in vitro.

The cytostatic effects of free retinal were compared with the cyclodextrin complex of retinal-carboxymethyldextran at concentrations lower than those causing cytotoxic effects, namely, below 2 and 40 $\mu M$, respectively. After 6 days of treatment the growth of the S-91 melanoma cells demonstrated dose-dependent inhibition (FIG. 2). Although retinal is indicated to be a more potent inhibitor than the corresponding complex at all concentrations where it is not toxic, the lower toxicity of the complex means that it can be used at higher concentrations than free retinal, and, consequently, a higher overall growth inhibition may be realized. The fact that the corresponding complex of tetradecanal exhibited no inhibitory effects at the same concentrations of aldehyde moiety, strongly indicates that the inhibitory effects of the retinal-dextran complex are due to the retinal moiety (Table 3). Furthermore, the reduced potency of combined retinal is apparently due to its covalent bond to carboxymethyldextran through the hydrazone link since the mere mixing of retinal with carboxymethyldextran hydrazide at the same proportions in which retinal is combined in the complex, fail to alter the activity of the retinal (Table 3).

Figure 3:
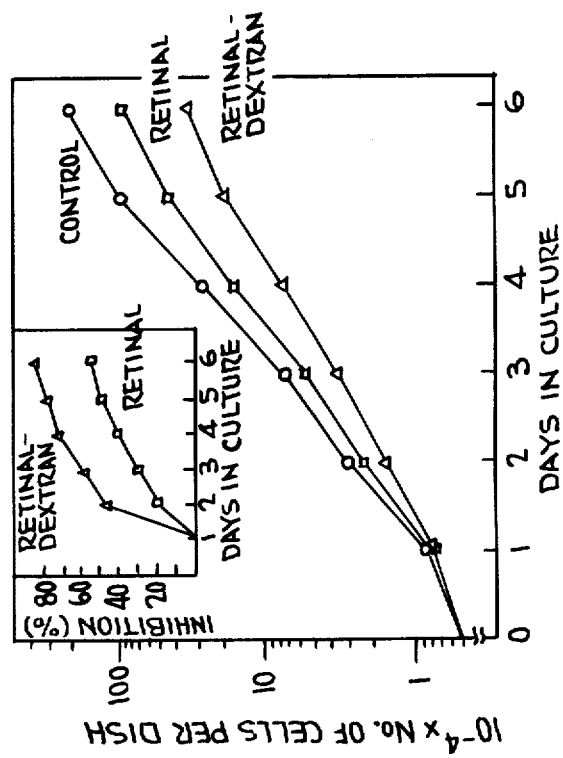
FIG. 3 graphically depicts the inhibition of growth of S-91 melanoma cell proliferation in the presence of retinal and dextrin-complexed retinal-dextran. The inset shown therein presents the same type of data comparing retinoic acid with a cyclodextrin-complexed polymer derivative of retinoic acid.

The time dependent course of the cytostatic effects of retinal (1 $\mu M$) and the retinal-carboxymethyldextran complex (10 $\mu M$ retinal moiety) are graphically presented in FIG. 3. There is no apparent inhibition of cell proliferation during the first 24 hours of exposure to either compound. After 48 hours, however, the growth rates of cells exposed to both the free compound and the complex were reduced in comparison to the untreated controls. Although the complex was added at a higher concentration than the free retinal, these dissimilar doses were chosen in order to emphasize that the lower potency of the complex (FIG. 2) is compensated for by its lower toxicity. This allows its use at higher doses than free retinal and thus causes greater growth inhibition.

Although biological testing of the non-polymer derivitized retinoids has not yet been undertaken, it is expected that these complexes will exhibit similar biological activity to the polymer derivitized complexes.

The embodiments of the invention in which an exclusive property or privilege is claimed are defined as follows:

1. A water soluble material comprising a cyclodextrin complex of the product formed by the reaction of a polymer and a retinoid, wherein said polymer contains polar or ionic functional groups.

2. A water soluble material comprising a cyclodextrin complex of a retinoid.

3. A water soluble material as claimed in claim 1 or claim 2, wherein the cyclodextrin is at least one member selected from the group consisting of $\alpha$-cyclodextrin, $\beta$-cyclodextrin, $\gamma$-cyclodextrin and methoxy, ethoxy and 2-hydroxyethoxy derivatives of the foregoing.

4. A water soluble material as claimed in claim 1 or claim 2, wherein the retinoid is selected from the group consisting of retinal, retinoic acid and derivatives of the foregoing which possess biological activity.

5. A water soluble material as claimed in claim 1, wherein the polymer is a member selected from the group consisting of polyamino acids, polyamino acid esters, polysaccharides, hydrophillic derivatives of polysaccharides and hydrazides of the foregoing.

6. A water soluble material as claimed in claim 5, wherein said polysaccharides are selected from the group consisting of polyamyloses and polyhexoses.

7. A water soluble material as claimed in claim 1, wherein said product is the carboxymethyldextran hydrazone of retinal.

8. A solution of the water soluble material of claim 1 or claim 2 in an aqueous medium.

9. A method of preparing a water soluble material comprising reacting the terminal group of at least one retinoid with those groups of a polymer capable of reacting with said terminal groups, and forming a complex with at least one cyclodextrin.

10. A method as claimed in claim 9, wherein said retinoid and said polymer are reacted in the presence of said at least one cyclodextrin.

11. A method as claimed in claim 9, wherein said terminal group is an aldehyde moiety and said those groups of a polymer are hydrazide moieties.

12. A method as claimed in claim 9, wherein said terminal group is a carboxyl moiety and said those groups of a polymer are amino moieties.

13. A method as claimed in claim 9, wherein said polymer is a polysaccharide.

14. A method as claimed in claim 9, wherein said polymer is a polyamino acid.

15. A method as claimed in claim 9, wherein said retinoid is retinal or a derivative thereof which possesses biological acitivity and said polymer is carboxymethyldextran containing at least one hydrazide group.

16. A method as claimed in claim 15, wherein said carboxymethyldextran is prepared by converting dextran to carboxymethyldextran which is subsequently converted to the polyhydrazide by reacting with hydrazine.

17. A method as claimed in claim 15, wherein said retinoid is retinoic acid or a derivative thereof and said polymer is a polyamino acid.

18. A method of making a water soluble material comprising complexing a retinoid and a cyclodextrin in an aqueous medium.

19. A method as claimed in claim 18 wherein said cyclodextrin is at least one member selected from the group consisting of $\alpha$-cyclodextrin, $\beta$-cyclodextrin, $\gamma$-cyclodextrin and ether type derivatives of the foregoing.

20. A method as claimed in claim 18 wherein said retinoid is selected from the group consisting of retinal, retinoic acid and derivatives of the foregoing.

21. A method of preparing solutions of a retinoid-cyclodextrin complex, comprising placing a retinoid and a cyclodextrin in an aqueous medium with stirring.

* * * * *